United States Patent [19]
Brimhall

[11] Patent Number: 5,584,810
[45] Date of Patent: Dec. 17, 1996

[54] NEEDLE POINT GUARD ASSEMBLY

[75] Inventor: Greg L. Brimhall, West Jordan, Utah

[73] Assignee: Becton Dickinson and Company, Franklin Lakes, N.J.

[21] Appl. No.: 500,719

[22] Filed: Jul. 11, 1995

[51] Int. Cl.$^6$ .................................................. A61M 5/00
[52] U.S. Cl. ........................... 604/110; 604/192; 604/263
[58] Field of Search ..................................... 604/192, 110, 604/187, 198, 263; 128/919

[56] References Cited

U.S. PATENT DOCUMENTS

| | | | |
|---|---|---|---|
| 5,322,517 | 6/1994 | Sircom et al. | 640/198 |
| 5,415,645 | 5/1995 | Friend et al. | 604/110 |

*Primary Examiner*—John D. Yasko
*Attorney, Agent, or Firm*—Eric M. Lee, Esq.

[57] ABSTRACT

A needle point guard assembly includes inner and outer housings disposed in nested relationship to one another to permit relative rotation therebetween. The proximal end walls of the inner and outer housings have apertures each of which is dimensioned to slidably receive a needle. The apertures are disposed in the housings such that they are registered in one rotational orientation of the housings relative to one another to define a first opening that allows a needle to pass therethrough. The needle point guard assembly further includes a spring for rotatably driving the housings relative to one another and a trigger for selectively holding the inner housing with respect to the outer housing in a rotational orientation where the apertures define the first opening. The trigger moves out of interfering relationship between the inner housing and the outer housing when the sharp distal tip of the needle is withdrawn into the needle point guard assembly. In this condition, the spring will rotatably drive the housings into orientations where the apertures will not be substantially aligned so that the overlapping area is smaller than the first opening. The edges of the apertures will thus bind against the needle and prevent further movement of the needle point guard assembly either proximally or distally along the needle.

21 Claims, 10 Drawing Sheets

NEEDLE POINT GUARD ASSEMBLY

BACKGROUND OF THE INVENTION

The present invention relates to a needle point guard assembly that can be slid relative to the needle so the sharp distal tip of the needle point is safely shielded inside the needle point guard assembly. When the sharp distal tip of the needle is safely shielded inside the needle point guard assembly, the needle point guard assembly lockingly engages the needle to prevent re-exposure of the sharp distal needle tip.

Sharp pointed needles are prevalent in health care institutions as part of, e.g., a syringe or intravenous (IV) catheter. The point at the distal end of the needle is used to penetrate tissue of a patient for administering drugs, extracting body fluids or placing an IV catheter in the patient. Accidental sticks of healthcare workers with a used needle may occur in certain emergency or other situations where a used needle is not properly disposed of. Such accidental needlesticks have become of greater concern recently because of diseases such as acquired immune deficiency syndrome, i.e. AIDS, and hepatitis that can be transmitted by the body fluids of an infected patient. As a result, a number of devices have been developed that purport to cover the sharp distal tip of a needle after use. Although some of these needle shielding devices work, there is still a need for needle shielding devices that are simple to use and effectively lock the sharp distal tip of the needle in the shield.

SUMMARY OF THE INVENTION

It is therefore an object of this invention to provide a needle shielding device that is simple to use and that effectively locks the sharp distal tip of the needle in the shield.

The needle point guard assembly of this invention includes nested inner and outer housings each having a generally tubular cross-section and a proximal end wall. The proximal end walls have apertures that slidably engage the outer cylindrical surface of the needle. However, the apertures are eccentrically disposed. The eccentricities of the apertures in the proximal end walls are such that in a first rotational orientation of the housings, the apertures register with one another. However, in a second rotational orientation of the housing, the apertures only partly register with one another. The needle point guard assembly further includes a trigger for releasably holding the inner and outer housings in a relative rotational position where the eccentric apertures are registered with one another. The trigger may be moved out of interfering relationship between the inner and outer housings to permit relative rotation between the inner and outer housings. The needle point guard assembly also includes a spring disposed between the inner and outer housings for rotating the housings relative to one another when the trigger has been moved out of interfering relationship between the inner and outer housings. The trigger maintains the inner housing "wound" with respect to the outer housing against the force of the spring when the sharp distal end of the needle extends beyond the distal tip of the guard and the trigger is in an interfering relationship between the inner and outer housings.

The needle point guard assembly is located about the needle so the sharp distal tip of the needle extends beyond the distal end of the guard during use. After such use, the needle point guard assembly may be slid relative to the needle to withdraw the sharp distal tip of the needle into the guard. This movement allows the trigger to move out of interfering relationship between the inner and outer housings. Upon such movement of the trigger, the spring rotates the inner and outer housings with respect to one another such that the initially registered eccentric apertures will move into unregistered positions relative to one another. This movement into unregistered alignments will effectively bind the proximal end walls of the inner and outer housings into tight clamping engagement with the outer cylindrical surface of the needle. This clamping engagement is maintained by the spring between the inner and outer housings. Thus, further axial movement of the needle point guard assembly relative to the needle in either direction is prevented.

BRIEF DESCRIPTION OF THE DRAWINGS

The above and other objects and advantages will be apparent upon consideration of the following drawings and detailed description. The preferred embodiments of the present invention are illustrated in the appended drawings in which like reference numerals refer to like elements and in which:

FIG. 5 is a cross-sectional view of the second embodiment of the needle point guard assembly of this invention taken along line 15—15 of FIG. 13;

DETAILED DESCRIPTION OF THE INVENTION

Figure 1:
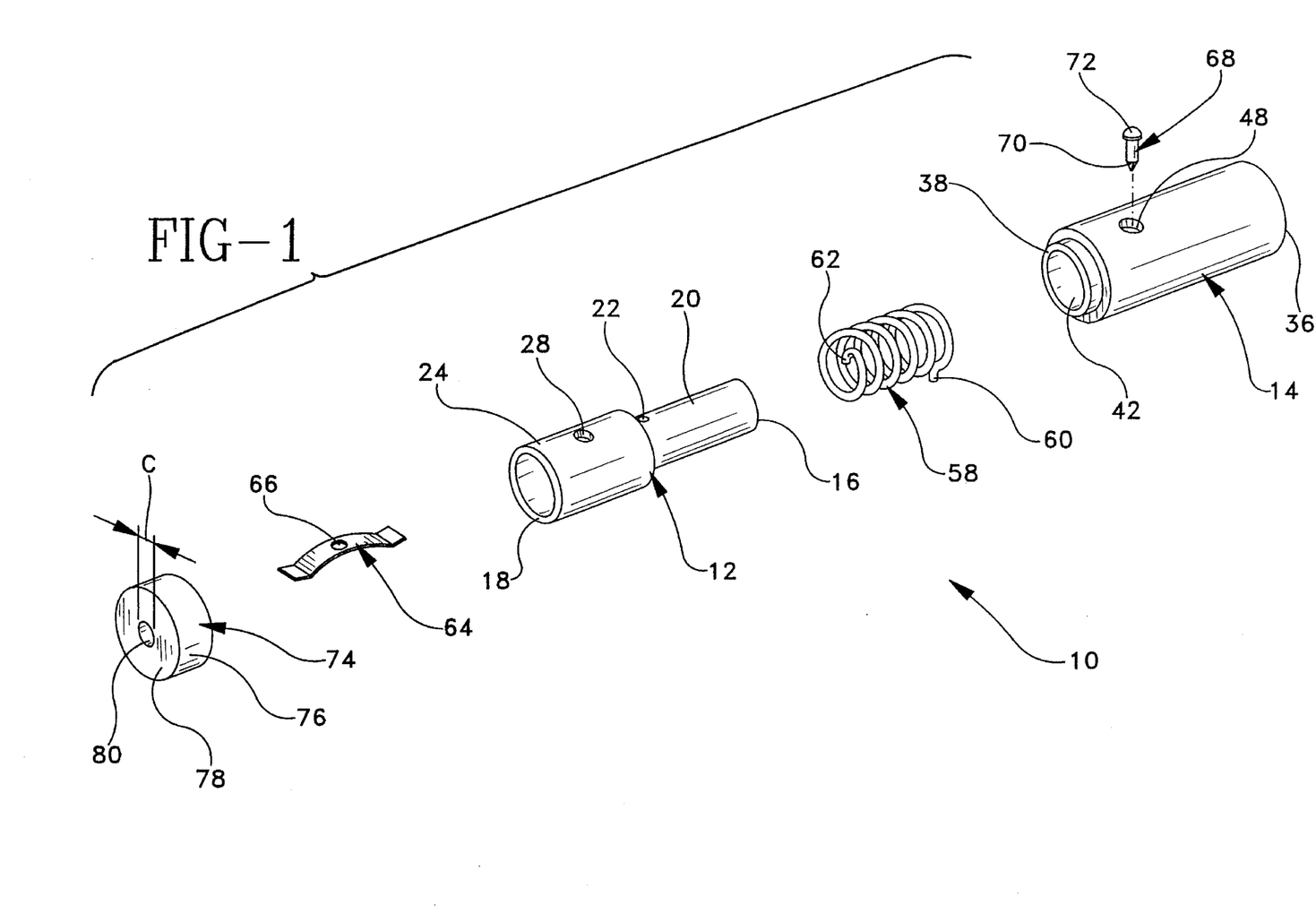
FIG. 1 is an exploded perspective view of a needle point guard assembly of this invention showing one embodiment of the trigger that holds the inner housing with respect to the outer housing prior to withdrawal of the needle into the assembly.

A needle point guard assembly in accordance with the subject invention is identified generally by the numeral 10 in FIG. 1. Assembly 10 includes generally tubular inner housing 12 and outer housing 14 that can be nested within one another as explained further herein.

Figure 2:
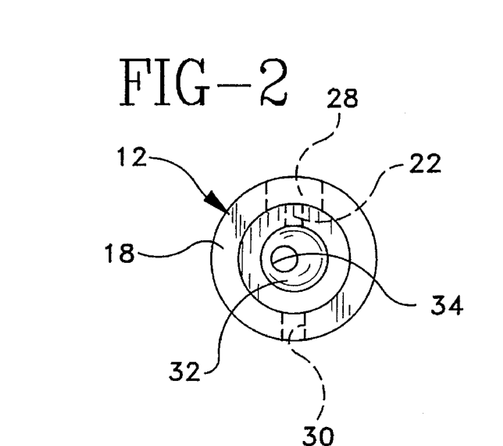
FIG. 2 is an end elevation view of the inner housing of the needle point guard assembly of this invention.
Figures 3, 5:
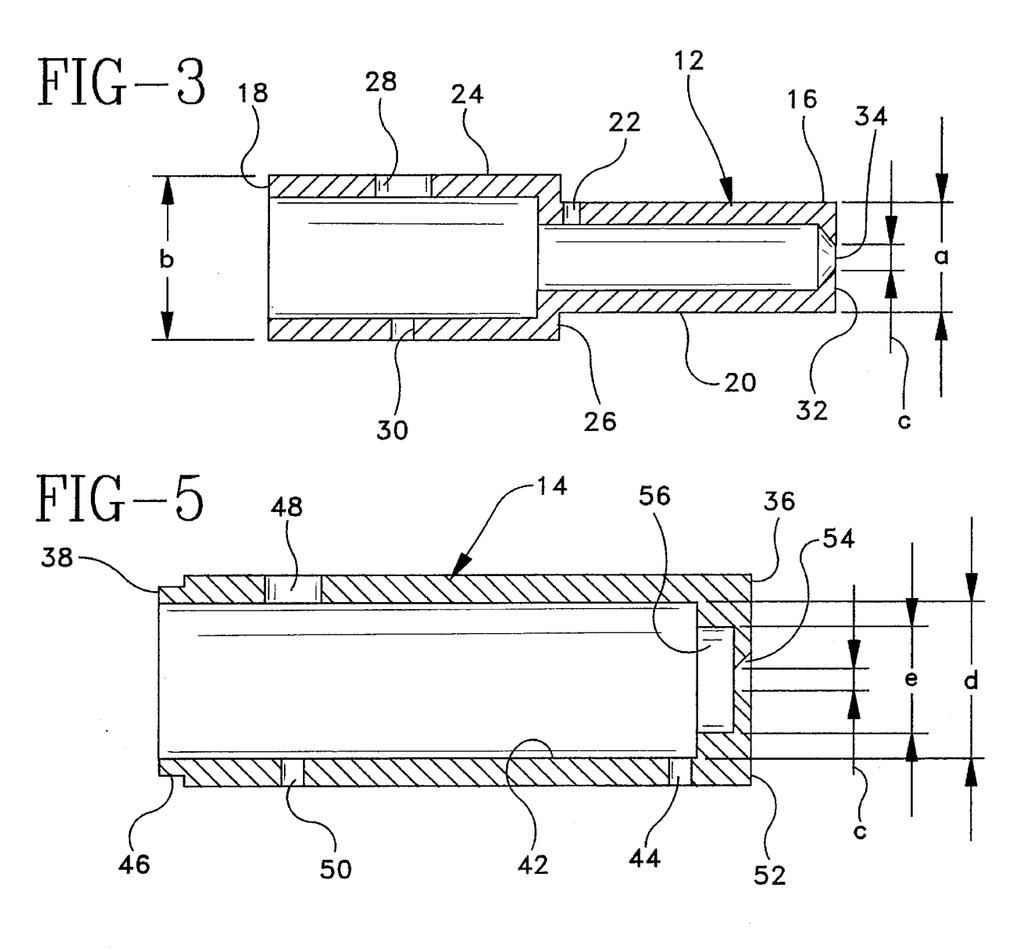
FIG. 3 is a cross-sectional view of the inner housing of the needle point guard assembly of this invention.
FIG. 5 is a cross-sectional view of the outer housing of the needle point guard assembly of this invention.

As shown in FIGS. 2 and 3, inner housing 12 includes opposed proximal end 16 and distal end 18. A proximal cylindrical portion 20 of outside diameter "a" extends distally from proximal end 16 of inner housing 12. A radially aligned aperture 22 extends through the sidewall of proximal cylindrical portion 20 at a location remote from proximal end 16.

Inner housing 12 further includes a cylindrical distal portion 24 extending from cylindrical proximal portion 20 to distal end 18 of inner housing 12. Cylindrical distal portion 24 is concentric with cylindrical proximal portion 20, but defines an outside diameter "b" which exceeds outside diameter "a." As a result, a step 26 is defined at the interface of cylindrical proximal portion 20 and cylindrical distal portion 24. Cylindrical distal portion 24 includes diametrically aligned apertures 28 and 30. Aperture 28 defines a diameter significantly greater than the diameter of aperture 30.

Distal end 18 of inner housing 12 is open. However, proximal end 16 of inner housing 12 includes a proximal end wall 32 having an aperture 34 extending therethrough. Aperture 34 defines a diameter "c" which exceeds the diameter of a needle to be used with needle point guard assembly 10. Portions of proximal end wall 32 surrounding aperture 34 are chamfered to form a well defined edge around aperture 34. As shown most clearly in FIG. 2, aperture 34 is eccentrically disposed with respect to concentric cylindrical proximal portion 20 and cylindrical distal portion 24.

Figure 4:
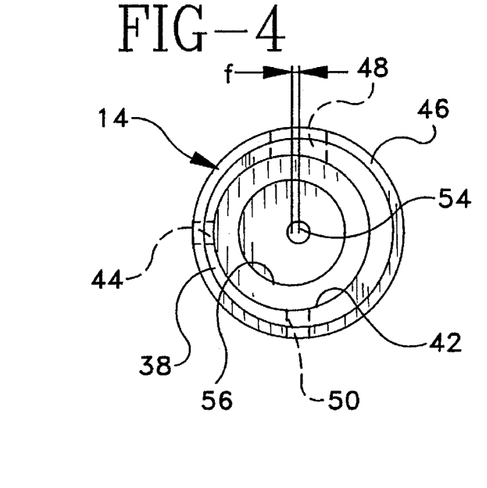
FIG. 4 is an end elevation view of the outer housing of the needle point guard assembly of this invention.

Outer housing 14 includes opposed proximal end 36 and distal end 38 and has a generally cylindrical cross-section. Distal end 38 of outer housing 14 is open. Outer housing 14 has a cylindrical interior surface 42 of diameter "d" which is slightly greater than outside diameter "b" of cylindrical distal portion 24 of inner housing 12. Interior surface 42 of outer housing 14 includes a slot 44 formed therein. In addition to the configuration of slot 44 shown in the FIGS., slot 44 can also extend longitudinally from distal end 38 to a location near proximal end 36 of outer housing 14. Slot 44 has a width approximately equal to the diameter of aperture 22 in inner housing 12. The distal, exterior surface regions of outer housing 14 define an undercut 46 for receiving a cap as explained further herein. Diametrically opposed apertures 48 and 50 extend through outer housing 14. Aperture 48 defines a diameter approximately equal to the diameter of aperture 28 in inner housing 12. Similarly, aperture 50 in outer housing 14 defines a diameter approximately equal to the diameter of aperture 30 in inner housing 12.

Proximal end 36 of outer housing 14 has a proximal end wall 52 having an aperture 54 of diameter "c" extending therethrough which is approximately equal to the diameter of aperture 34. Portions of proximal end wall 52 surrounding aperture 54 are chamfered to form a well defined edge around aperture 54. Outer housing 14 also defines an undercut cylindrical seat 56 having a diameter "e" slightly greater than outside diameter "a" of cylindrical proximal portion 20 of inner housing 12.

As shown most clearly in FIG. 4, aperture 54 in end wall 52 is concentrically disposed with respect to the outside surface of outer housing 14. Additionally, cylindrical seat 56 and inner cylindrical surface 42 are concentrically disposed with respect to one another. However, aperture 54 is eccentrically disposed with respect to cylindrical seat 56 and inner cylindrical surface 42. The magnitude of this eccentricity, as indicated by dimension "f" in FIG. 4, is substantially equal to the eccentricity of aperture 34 in inner housing 12.

Inner housing 12 can be slidably inserted into outer housing 14 such that cylindrical proximal portion 20 is rotatably disposed in cylindrical seat 56 of outer housing 14 and such that cylindrical distal portion 24 of inner housing 12 is rotatably disposed against inner surface 42 of outer housing 14.

Needle point guard assembly 10 further includes a cap 74 having a short cylindrical side wall 76 dimensioned to mount on undercut seat 46 of outer housing 14. Cap 74 further includes an end wall 78 with a central aperture 80 extending centrally therethrough. Aperture 80 defines a diameter "c" slightly greater than the diameter of the needle to be used with needle point guard assembly 10 and approximately equal to the diameter of apertures 34 and 54.

Figure 6:
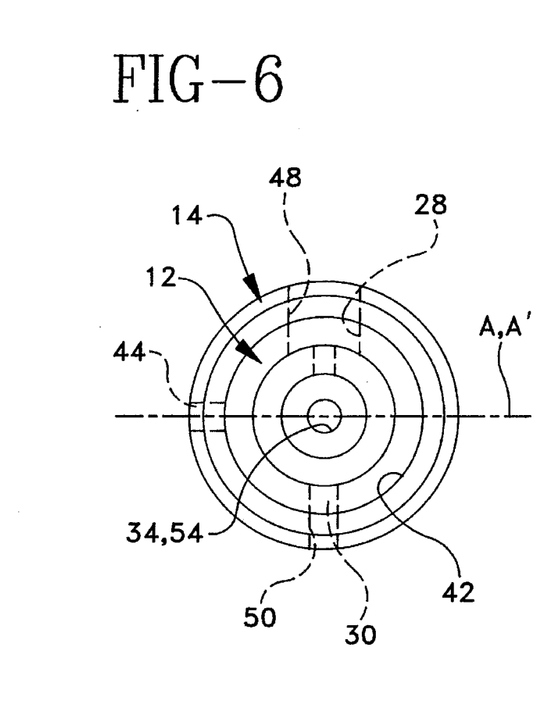
FIG. 6 is an end elevation view of the assembled inner and outer housings of the needle point guard assembly of this invention in a first relative rotational orientation therebetween.
Figure 7:
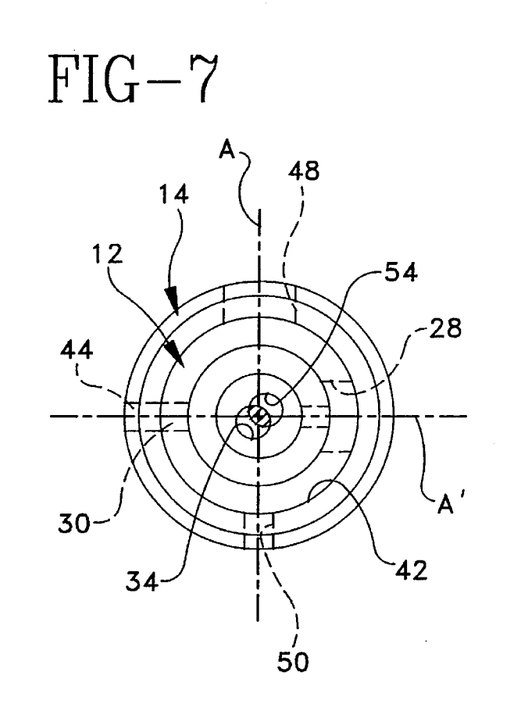
FIG. 7 is an end elevation view similar to FIG. 6, but showing a second relative rotational orientation.
Figure 8:
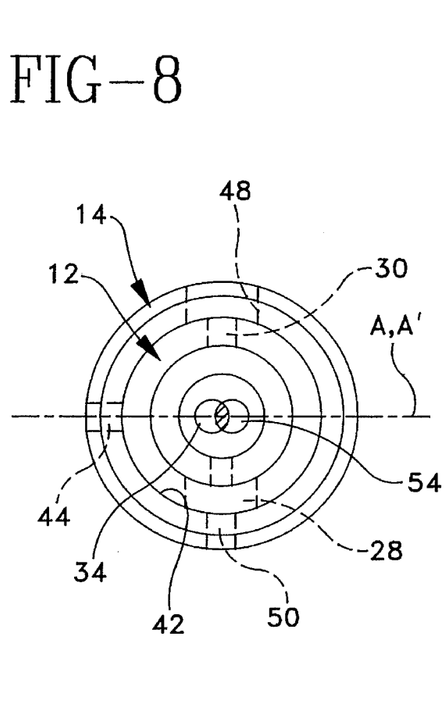
FIG. 8 is an end elevation view similar to FIGS. 6 and 7, but showing a third relative rotational orientation.
Figure 9:
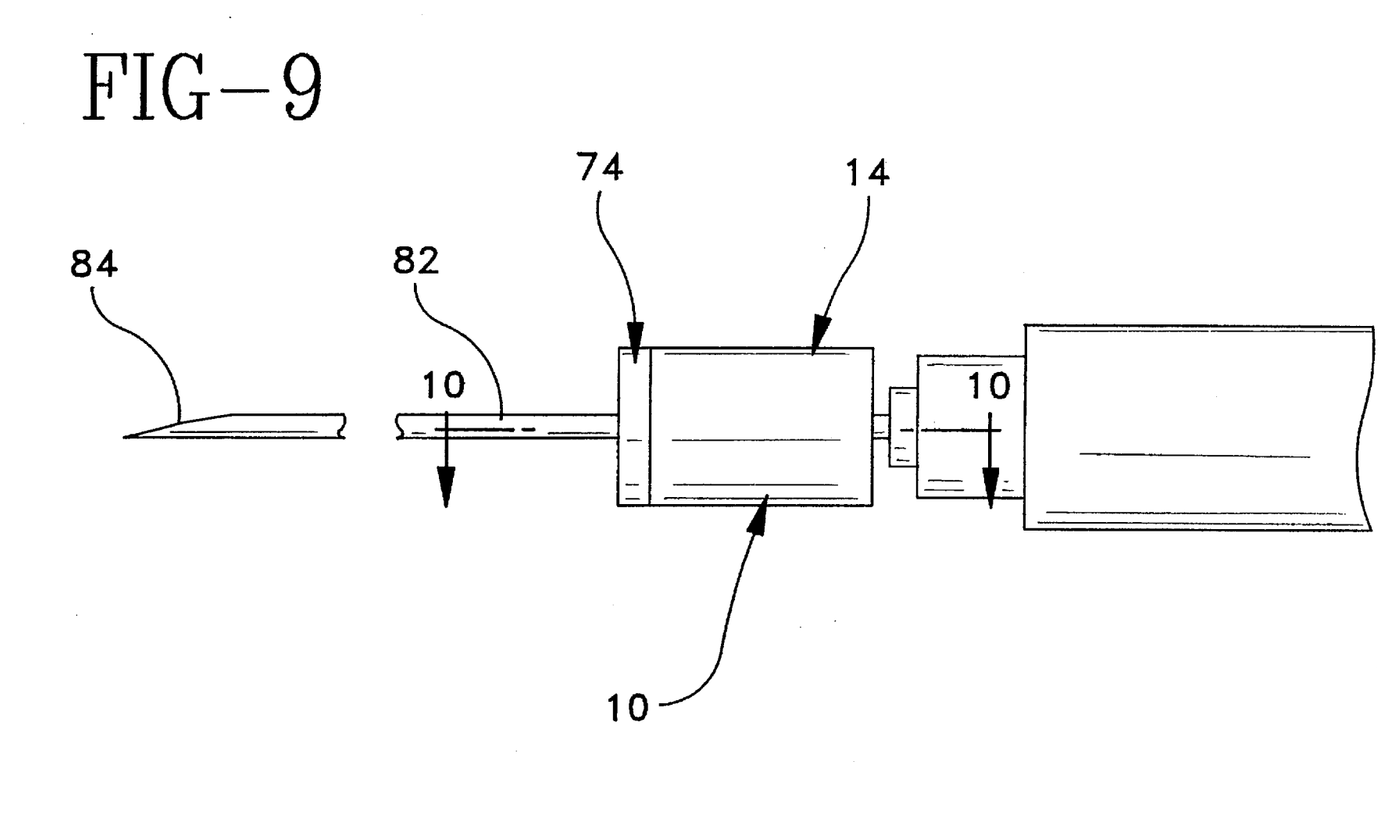
FIG. 9 is a side elevation view of the needle point guard assembly of this invention mounted on a needle prior to withdrawal of the needle into the assembly.

Inner housing 12 and outer housing 14 will have one rotational orientation where apertures 34 and 54 are perfectly registered, as shown in FIG. 6. In this orientation, apertures 28, 30, 48 and 50 also will lie on a common axis. A 90° rotation of either inner housing 12 or outer housing 14 to the FIG. 7 orientation causes apertures 34 and 54 to be only partly registered with one another. These registered portions of apertures 34 and 54 will define a cross-sectional dimension which is less than the diameter "c" of apertures 34 and 54. A 180° rotation of inner housing 12 or outer housing 14 from the FIG. 6 orientation to the FIG. 8 orientation, causes apertures 34 and 54 to be even less registered. In this condition, the cross-sectional dimension of the registered portions of apertures 34 and 54 is less than the cross-sectional dimension of the registered portions of apertures 34 and 54 depicted in FIG. 7. Further rotation of either housing will bring apertures 34 and 54 back into closer registration with one another. The minimum cross-sectional dimension shown in FIG. 8 is significantly less than the diameter of a needle to be used with needle point guard assembly 10. Thus, at some rotational orientation between the FIG. 6 condition and the FIG. 8 condition, the well defined edges of apertures 34 and 54 can be brought into secure gripping engagement with the outer surface of the needle.

Returning to FIG. 1, needle point guard assembly 10 further includes a coil spring 58 having a proximal end 60 formed into a radially outward alignment and a distal end 62 formed into a radially inward alignment. The wire from which coil spring 58 is formed defines a diameter less than the diameter of aperture 22 in cylindrical proximal portion 20 of inner housing 12 and less than the width of slot 44 in outer housing 14. Coil spring 58 defines an inside diameter slightly greater than outside diameter "a" of cylindrical proximal portion 20 of inner housing 12. Additionally, coil spring 58 defines an outside diameter slightly less than the inside diameter "d" of outer housing 14.

Coil spring 58 is slidably mounted over cylindrical proximal portion 20 of inner housing 12 such that radially aligned distal end 62 of coil spring 58 is engaged in aperture 22 that extends through the side wall of cylindrical proximal portion 20. Inner housing 12 and coil spring 58 are then slidably inserted into outer housing 14, such that cylindrical proximal portion 20 of inner housing 12 is rotatably positioned in seat 56 of outer housing 14. This slidable engagement is achieved by aligning proximal end 60 of coil spring 58 with slot 44 of outer housing 14. It will be appreciated that relative rotation of inner housing 12 and outer housing 14 will require a biasing of coil spring 58.

Figure 10:
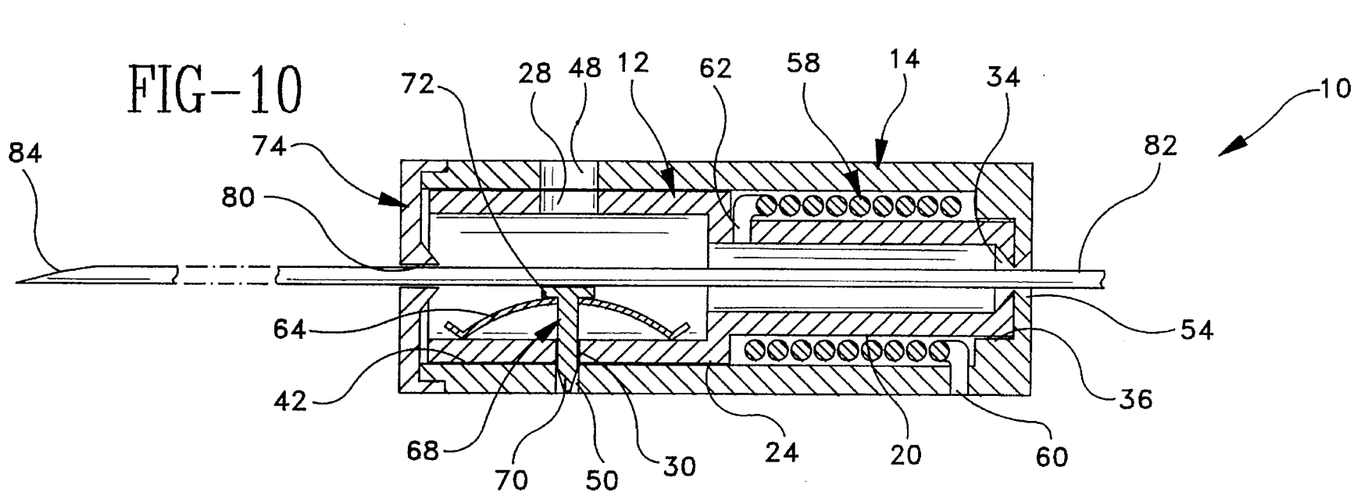
FIG. 10 is a cross-sectional view of the needle point guard assembly of this invention taken along line 10—10 in FIG. 9.
Figure 11:
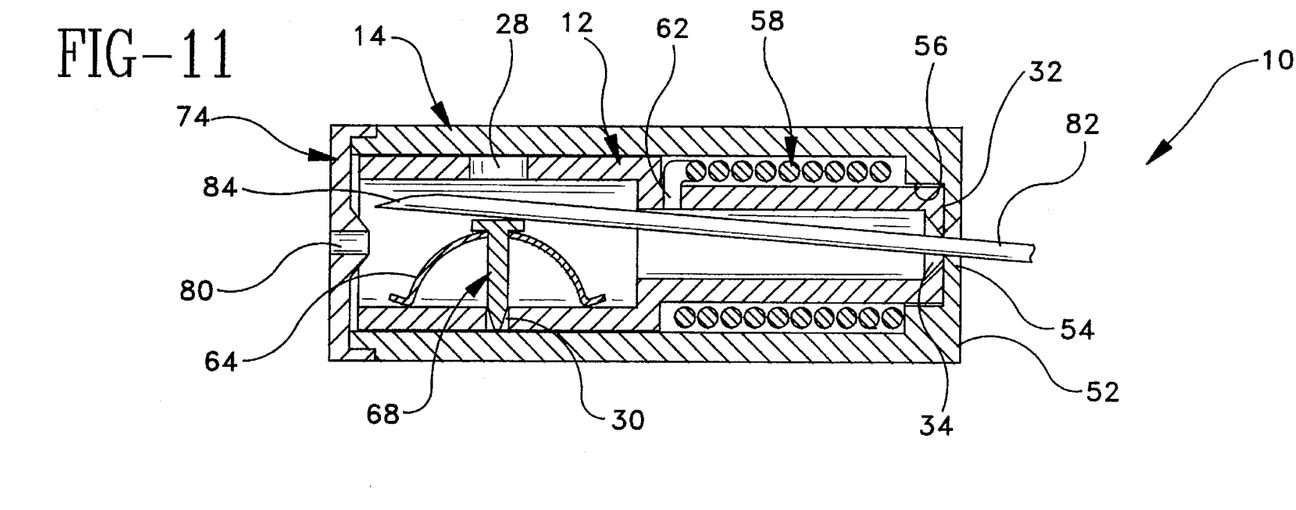
FIG. 11 is a cross-sectional view similar to FIG. 10, but showing the needle point guard assembly of this invention in shielding engagement around the sharp distal tip of the needle.
Figure 12:
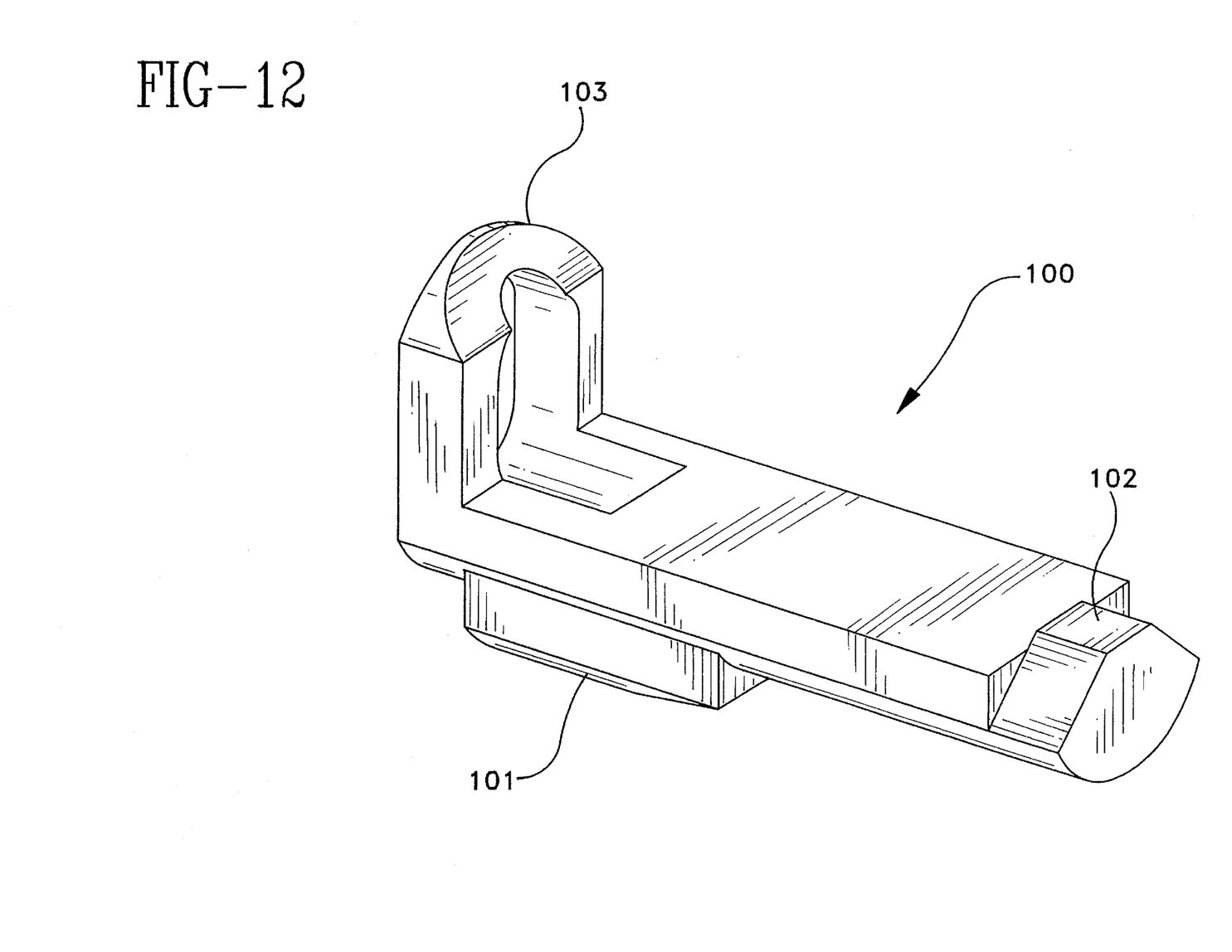
FIG. 12 is a perspective view of the second embodiment of the trigger that holds the inner housing with respect to the outer housing prior to withdrawal of the needle into the assembly.

Needle point guard assembly 10 further includes a trigger to maintain inner housing 12 "wound" with respect to outer housing 14 when the sharp distal end of the needle extends beyond the distal end of assembly 10. This trigger must also allow inner housing 12 to "unwind" with respect to outer housing 14 when the distal end of the needle is withdrawn into assembly 10. One embodiment of the trigger is shown in FIGS. 1, 10 and 11.

In the first embodiment of the trigger, the trigger includes a leaf spring 64 and an anchor pin 68. Leaf spring 64 is dimensioned to fit within cylindrical distal portion 24 of inner housing 12. Leaf spring 64 includes a central aperture 66 extending therethrough and has a diameter approximately equal to the diameters of apertures 30 and 50 in inner housing 12 and outer housing 14 respectively. Although a leaf spring is preferred, any other type of spring could be used. Anchor pin 68 is provided with an elongate shank 70 and a head 72. Shank 70 defines a diameter slightly less than the diameters of aperture 66 in leaf spring 64 and apertures 30 and 50 in inner housing 12 and outer housing 14 respectively. Head 72 of anchor pin 68 defines a diameter greater than the diameters of apertures 66, 30 and 50 and slightly less than the diameters of apertures 28 and 48 in inner housing 12 and outer housing 14 respectively.

With inner housing 12 nested inside outer housing 14 and rotated with respect thereto, apertures 34 and 54 will be registered as shown in FIG. 6. This will also register apertures 28, 30, 48 and 50. Leaf spring 64 is placed in inner housing 12 such that aperture 66 is registered with apertures 30 and 50.

Anchor pin 68 then is passed through registered apertures 28 and 48 such that shank 70 passes through aperture 66 of leaf spring 64 and through aperture 30 of inner housing 12. A flattening deflection of leaf spring 64 via a rod (not shown) extending through apertures 28 and 48 will permit shank 70 to enter aperture 50 of outer housing 14. In this condition, shank 70 of anchor pin 68 locks inner housing 12 and outer housing 14 in a fixed rotational orientation in which coil spring 58 is loaded. Cap 74 then is securely mounted to undercut 46 at distal end 38 of outer housing 14 to complete assembly 10.

Assembly 10 can be mounted to a needle 82 by merely urging sharp distal tip 84 of needle 82 through registered apertures 34 and 54 in the proximal end of assembly 10 and then through aperture 80 in cap 74. As noted above, aperture 54 is concentric with the outer surface of outer housing 14, and aperture 80 is concentric with cap 74 Hence assembly 10 will be axially disposed on needle 82 as shown in FIG. 10. The resiliency of leaf spring 64 will urge head 72 of anchor pin 68 against the outer surface of needle 82 to prevent unintended sliding of assembly 10 along needle 82. Simultaneously, needle 82 will ensure that shank 70 of anchor pin 68 remains in both apertures 30 and 50 to prevent relative rotation between inner housing 12 and outer housing 14.

After use of needle 82, needle point guard assembly 10 can be slid distally with respect to needle 82. Sufficient relative movement will cause cap 74 to pass distally beyond sharp distal tip 84 of needle 82. Thus, cap 74 will no longer support needle 82, and leaf spring 64 will resiliently move toward the unbiased condition shown in FIG. 11. Leaf spring 64 will drive anchor pin 68 into needle 82, and will urge needle 82 into an orientation offset from aperture 80 in cap 74. In this position, any distally directed forces on needle point guard assembly 10 will merely urge sharp distal tip 84 of needle 82 into cap 74, and will prevent re-exposure of needle 82. Leaf spring 64 is not critical to the operation of the first embodiment of the trigger. As discussed below in connection with the second embodiment of the trigger, torsional forces on shank 70 urge pin 68 out of engagement with aperture 50 without the necessity of leaf spring 64 when needle 82 has been withdrawn into needle point guard assembly 10.

Once anchor pin 68 has moved so that shank 70 is displaced from aperture 50 in outer housing 14, inner housing 12 will rotate under forces exerted by coil spring 58 when the user holds outer housing 14. This rotational driving of inner housing 12 relative to outer housing 14 by coil spring 58 causes apertures 34 and 54 to move from the registered condition depicted in FIG. 6 and toward the unregistered conditions depicted in FIGS. 7 or 8. As noted above, the misalignment of eccentric apertures 34 and 54 substantially reduces the cross-sectional dimensions of registered portions of apertures 34 and 54. Hence, the well defined edges of apertures 34 and 54 are driven into secure biting engagement with outer circumferential surface regions of needle 82 to prevent either proximal or distal movement of needle point guard assembly 10.

Figure 13:
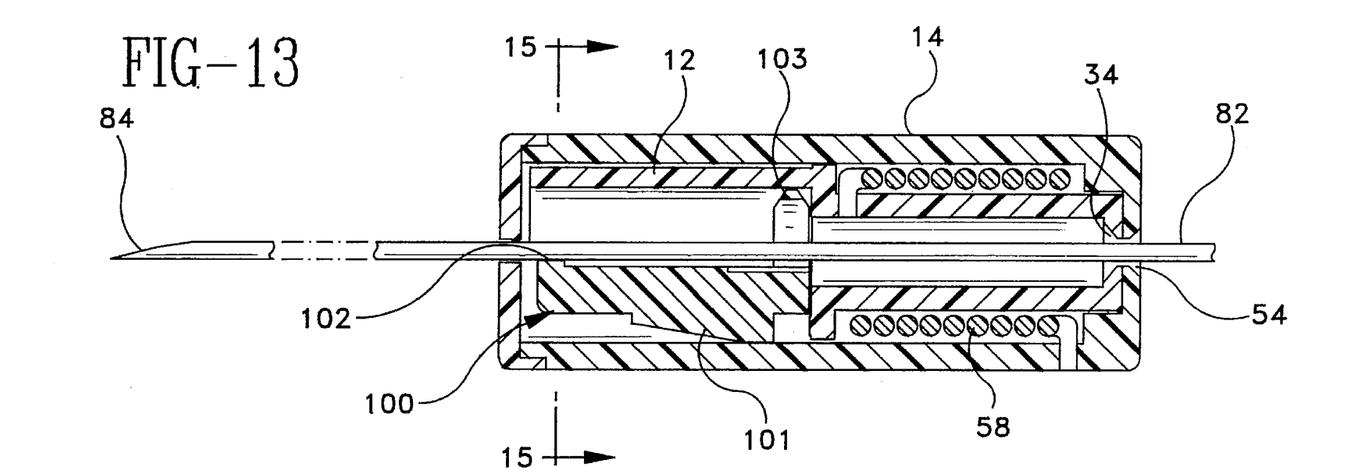
FIG. 13 is a cross-sectional view of the needle point guard assembly of the invention with the second embodiment of the trigger prior to withdrawal of the needle into the assembly.
Figure 14:
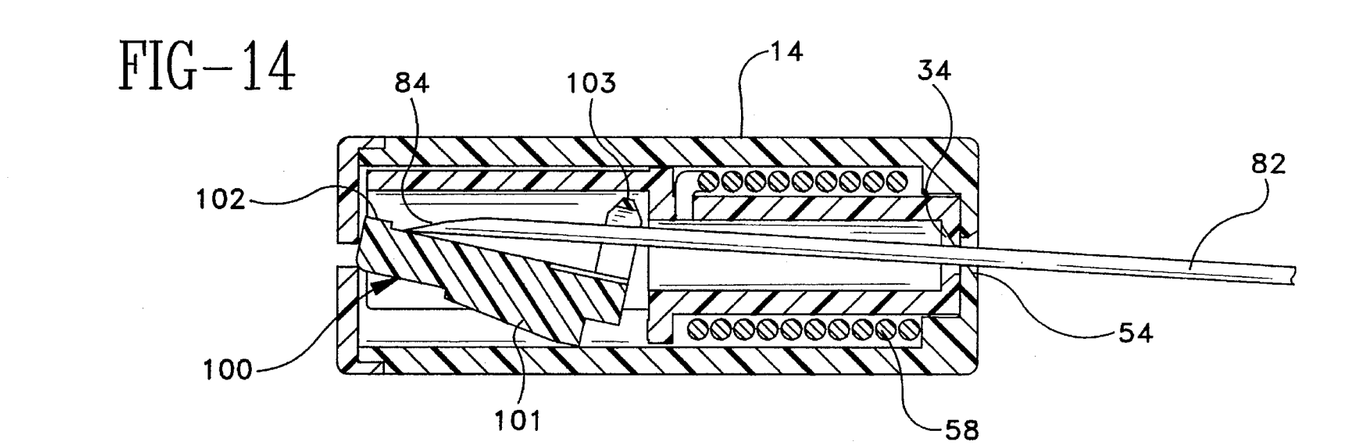
FIG. 14 is a cross-sectional view of the needle point guard assembly of this invention with the second embodiment of the trigger in shielding engagement around the sharp distal tip of the needle.
Figure 15:
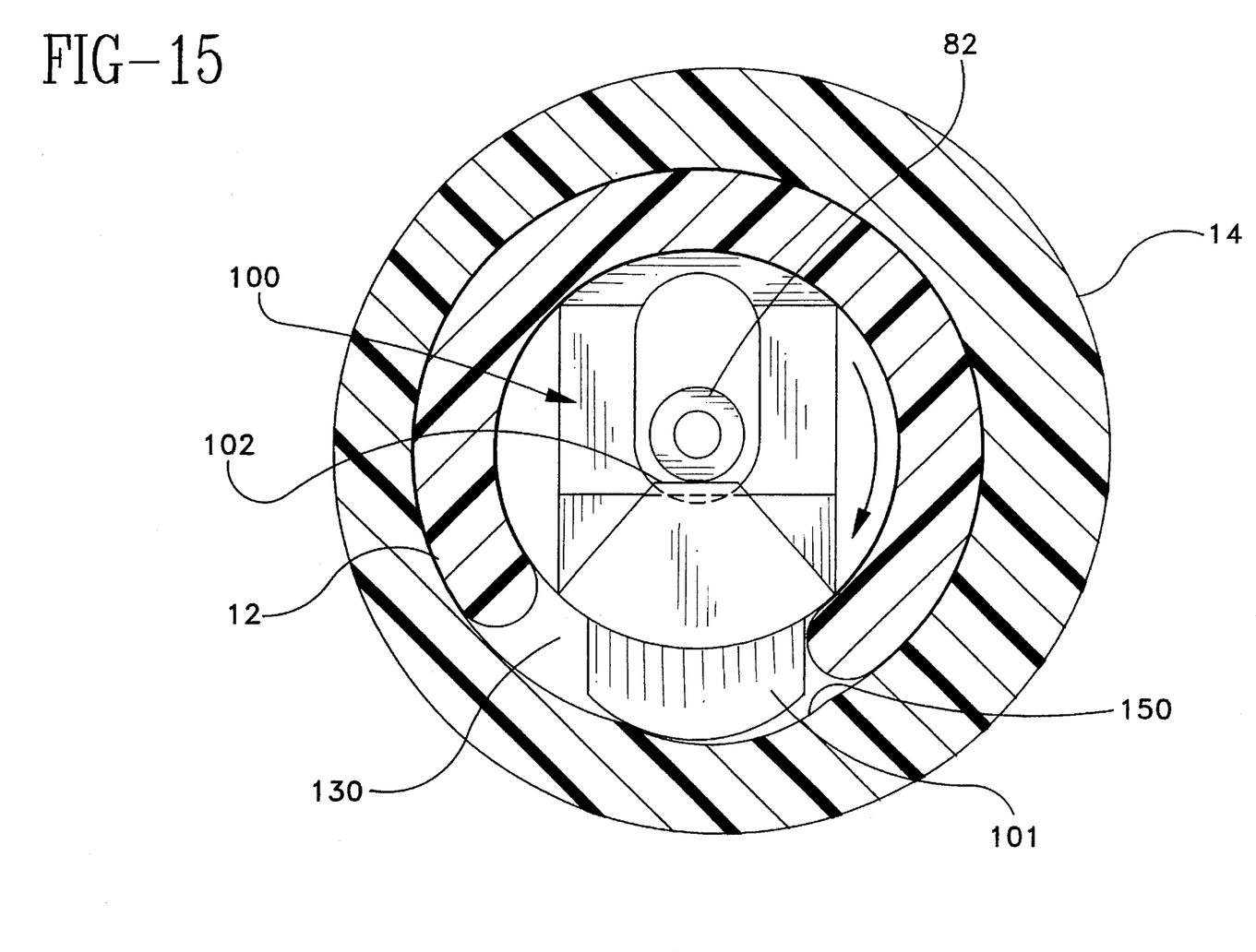

A different trigger instead of the anchor pin 68 and leaf spring 64 of the first embodiment of the trigger can be used. The second and preferred embodiment of the trigger is shown in FIGS. 12–15. The trigger 100 includes a trigger tang 101 and a needle sensing tang 102 located adjacent opposite ends of trigger 100. Trigger tang 101 interferes with the rotation of inner housing 12 with respect to outer housing 14 until it is moved out of this interfering relationship as described more fully below. As shown in FIG. 13, needle sensing tang 102 maintains trigger tang 101 in the interfering relationship with inner housing 12 and outer housing 14 until sharp distal tip 84 of needle 82 is withdrawn into assembly 10.

Inner housing 12 defines an opening 130 therein to allow trigger tang 101 to pass through. A portion of the inner wall of outer housing 14 defines a cut-out 150. This cut out 150 is oriented so that when inner housing 12 is wound against the force of spring 58, opening 130 in inner housing 12 is aligned with cut-out 150 of outer housing 14 when aperture 34 is aligned with aperture 54. Trigger tang 101 can thus fit through opening 130 and extend into cut-out 150 to prevent spring 58 from "unwinding" inner housing 12 with respect to outer housing 14. Preferably the bottom surface of trigger tang 101 that engages cut-out 150 of outer housing 14 has an arcuate surface. The radius of curvature of this surface preferably should have the same or smaller radius of curvature than the surface of cut-out 150. This relative radius of curvature facilitates movement of trigger tang 101 out of interfering relationship with cut-out 150 when needle sensing tang 102 is no longer in engagement with needle 82.

The torsional force exerted on trigger tang 101 by inner housing 12 due to spring 58 includes a force component that urges trigger tang 101 up out of cut-out 150. By positioning trigger 100 so needle sensing tang 102 abuts needle 82, trigger 100 can remain in its interfering position as long as needle 82 opposes the upward force exerted by inner housing 12. However, once sharp distal tip 84 of needle 82 is withdrawn into assembly 10, trigger 100 will be forced out of its interfering position allowing inner housing 12 to rotate with respect to outer housing 14 and lock sharp distal tip 84 of needle 82 inside assembly 10 as described above It is important for trigger 100 to include a pivot tang 103 that is offset from trigger tang 101. This offset allows trigger 100 to be forced out of its interfering position allowing inner housing 12 to rotate with respect to outer housing 14. Preferably pivot tang 103 should be offset from trigger tang by about 0.010 inches to about 0.125 inches. In addition, needle sensing tang 102 should be offset from trigger tang 101 to ensure that the upwardly directed force causes trigger 100 to pivot and move trigger tang 101 out of cut-out 150. Preferably needle sensing tang 102 should be offset from trigger tang 101 by about 0.10 inches to about 0.50 inches. Pivot tang 103 abuts the inner surface of inner housing 12 to stabilize trigger 100 in inner housing 12. It also provides a pivot point about which trigger 100 can pivot once needle 82 is withdrawn into assembly 10.

Figure 16:
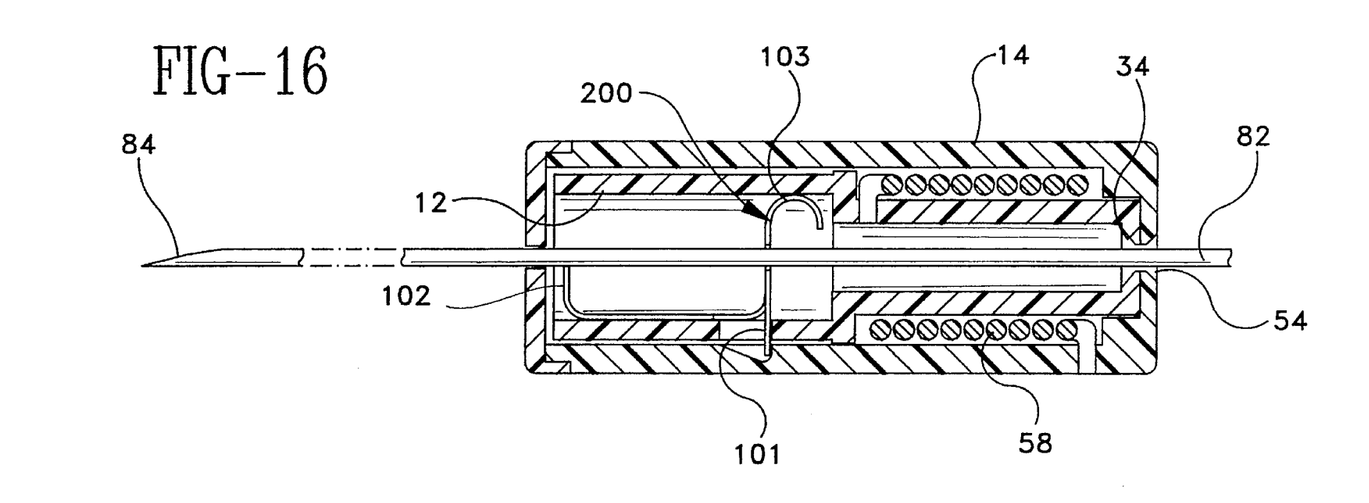
FIG. 16 is a cross-sectional view of the needle point guard assembly of this invention with the third embodiment of the trigger prior to withdrawal of the needle into the assembly.
Figure 17:
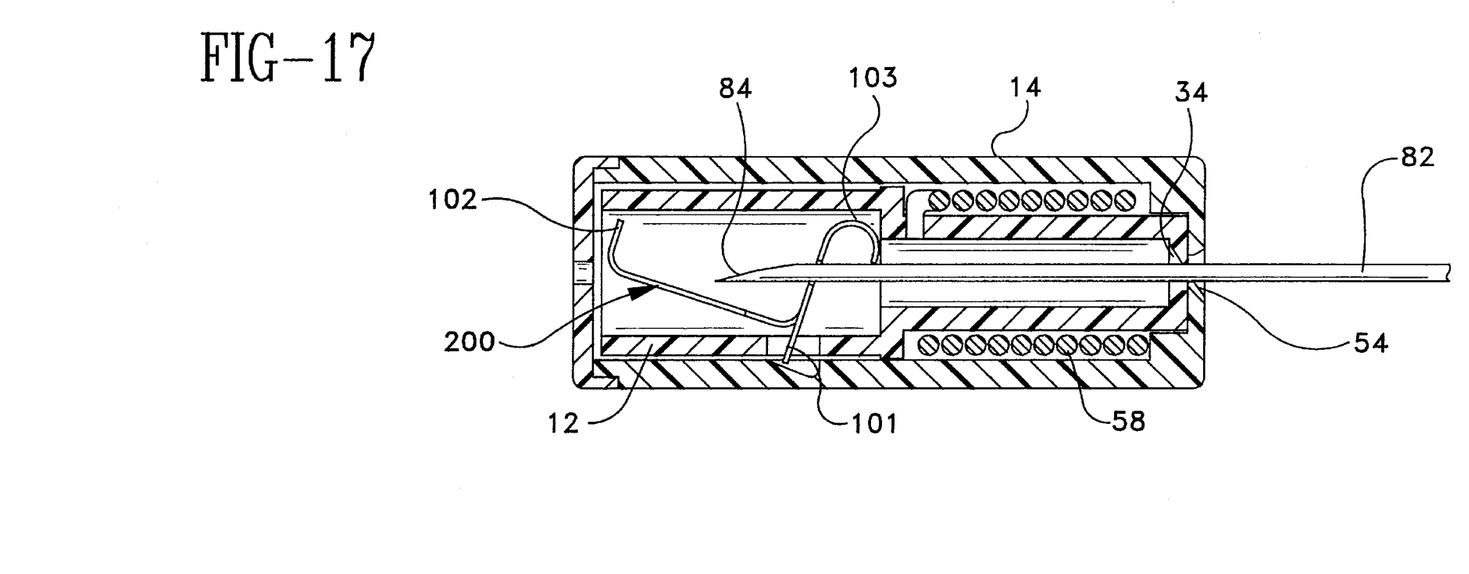
FIG. 17 is a cross-sectional view of the needle point guard assembly of this invention with the third embodiment of the trigger in shielding engagement around the sharp distal tip of the needle.
Figure 18:
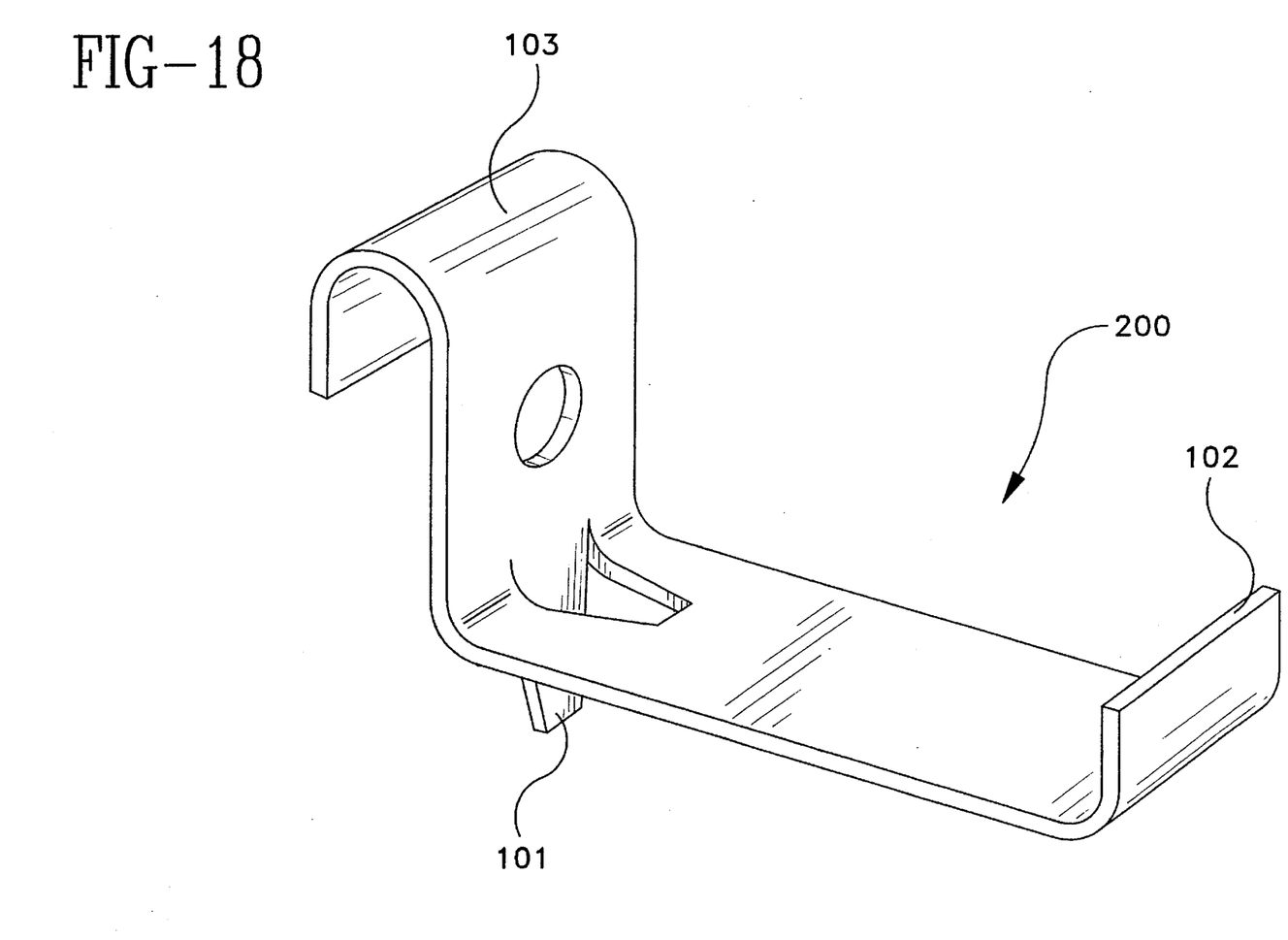
FIG. 18 is a perspective view of the third embodiment of the trigger that holds the inner housing with respect to the outer housing prior to withdrawal of the needle into the assembly.

A third embodiment of the trigger is shown in FIGS. 16–18. This embodiment is substantially the same as and functions in substantially the same manner as the embodiment shown in FIGS. 12–15. The third embodiment of the trigger 200 includes a trigger tang 101, a needle sensing tang 102 and a pivot tang 103.

Thus it is seen that a needle point guard is provided that is easy to use and that effectively locks the sharp distal tip of the needle in the shield.

I claim:

1. A needle point guard assembly, comprising:
   an outer housing having a proximal end wall defining a first aperture extending through said proximal end wall; and
   an inner housing rotatably supported within the outer housing and having a proximal end wall defining a second aperture extending therethrough, such that in a first rotational orientation of the inner housing and the outer housing, the first aperture and the second aperture are in substantial alignment to define a first opening, and such that in other rotational orientations of the inner housing and the outer housing, the first aperture and the second aperture define an overlapping portion smaller than the first opening.

2. The needle point guard assembly of claim 1, further comprising a spring operably connected to the inner housing and the outer housing.

3. The needle point guard assembly of claim 2, further comprising a distal cap mounted to a selected one of the inner housing and the outer housing, the cap having a third aperture extending axially therethrough.

4. The needle point guard assembly of claim 1, wherein the outer housing has a first longitudinal axis and the first aperture is aligned with the first longitudinal axis.

5. The needle point guard assembly of claim 4, wherein the inner housing has a second longitudinal axis and the second aperture is offset from the second longitudinal axis.

6. The needle point guard assembly of claim 5, further comprising a spring operably connected to the inner housing and the outer housing.

7. The needle point guard assembly of claim 6, further comprising a distal cap mounted to a selected one of the inner housing and the outer housing, the cap having a third aperture extending axially therethrough.

8. The needle point guard assembly of claim 1, further comprising a trigger disposed in the inner housing and movable to extend between the inner housing and the outer housing selectively to prevent relative rotation between the outer housing and the inner housing.

9. The needle point guard assembly of claim 8, further comprising a spring operably connected to the inner housing and the outer housing.

10. The needle point guard assembly of claim 9, further comprising a distal cap mounted to a selected one of the inner housing and the outer housing, the cap having a third aperture extending axially therethrough.

11. The needle point guard assembly of claim 1, further comprising a means for imparting relative rotational movement between the inner housing and the outer housing.

12. The needle point guard assembly of claim 11, further comprising a means for selectively preventing relative rotational movement between the inner housing and the outer housing.

13. A needle point guard assembly, comprising:
   an outer housing having an outer wall and a proximal end wall defining a first aperture extending through said proximal end wall;
   an inner housing rotatably supported within the outer housing and having an outer wall and a proximal end wall defining a second aperture extending therethrough such that in a first rotational orientation of the inner housing and the outer housing, the first aperture and the second aperture are in substantial alignment to define a first opening, and such that in other rotational orientations of the inner housing and the outer housing, the first aperture and the second aperture define an overlapping portion smaller than the first opening;
   a spring operably connected to the inner housing and the outer housing; and
   a trigger disposed in the inner housing and movable between a first position where the trigger prevents relative rotation between the inner housing and the outer housing in the first rotational orientation and a second position where the trigger allows relative rotation between the inner housing and the outer housing.

14. The needle point guard assembly of claim 13 wherein the inner housing defines a third aperture in the outer wall, the outer housing defines a cut out in the outer wall and the trigger includes a trigger tang that extends through the third aperture and into the cut out in the first rotational orientation.

15. The needle point guard assembly of claim 14 wherein the trigger includes a needle sensing tang and a pivot tang both of which are axially offset from the trigger tang.

16. The needle point guard assembly of claim 14 wherein the cut out has a surface with a radius of curvature and the trigger tang defines a lower surface having a radius of curvature which is the same as or less than the radius of curvature of the cut out surface.

17. The needle point guard assembly of claim 14 wherein the trigger further includes a spring for urging the trigger tang out of the cut out.

18. A needle point guard assembly, comprising:
   an outer housing defining a cut out therein;

an inner housing defining an aperture therein and being rotatably supported within the outer housing; and a trigger disposed in the inner housing and including a trigger tang that is movable to extend through the aperture in the inner housing and into the cut out of the outer housing selectively to prevent relative rotation between the outer housing and the inner housing.

19. The needle point guard assembly of claim 18 wherein the trigger includes a needle sensing tang and a pivot tang both of which are axially offset from the trigger tang.

20. The needle point guard assembly of claim 18 wherein the cut out has a surface with a radius of curvature and the trigger tang defines a lower surface having a radius of curvature which is the same as or less than the radius of curvature of the cut out surface.

21. The needle point guard assembly of claim 18 wherein the trigger further includes a spring for urging the trigger tang out of the cut out.

\* \* \* \* \*